United States Patent [19]

Tóth et al.

[11] 4,136,189
[45] Jan. 23, 1979

[54] 2-(5-NITRO-FURFURYLIDENE)-AMINO-BENZIMIDOLES AND FUNGICIDAL COMPOSITIONS CONTAINING THE SAME

[75] Inventors: Géza Tóth; István Tóth, both of Budapest, Hungary

[73] Assignee: Chinoin Gyógyszer és Vegyészeti Termékek Gyára R.T., Budapest, Hungary

[21] Appl. No.: 722,087

[22] Filed: Sep. 10, 1976

[30] Foreign Application Priority Data

Sep. 16, 1975 [HU] Hungary .................. CI 1605

[51] Int. Cl.² .................. C07D 405/12; A61K 31/415
[52] U.S. Cl. .................. 424/273 R; 542/406
[58] Field of Search .................. 260/309.2, 240 A; 424/273; 242/406

[56] References Cited

U.S. PATENT DOCUMENTS

| 3,401,171 | 9/1968 | Craig et al. | 260/309.2 |
| 3,401,173 | 9/1968 | Chow et al. | 260/309.2 |
| 3,920,682 | 11/1975 | Roder et al. | 260/309.2 |
| 3,926,967 | 12/1975 | Hawgwitz et al. | 260/240 A |
| 3,978,075 | 8/1976 | Toth et al. | 260/309.2 |

FOREIGN PATENT DOCUMENTS

| 1523597 | 3/1968 | France | 260/309.2 |
| 39-15143 | 7/1964 | Japan | 260/240 A |
| 45-8419 | 3/1970 | Japan | 260/240 A |
| 45-25093 | 8/1970 | Japan | 260/240 A |

OTHER PUBLICATIONS

Kada et al., Chem. Abst. 1968, vol. 69, No. 86905h.
Simonov et al., Chem. Abst. 1965, vol. 63, cols. 8343-8344.

Primary Examiner—Natalie Trousof
Attorney, Agent, or Firm—Karl F. Ross

[57] ABSTRACT

A fungicidal composition contains as an active ingredient a compound of the formula

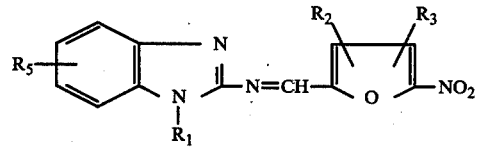

wherein $R_1$ is hydrogen or a carbamoyl group, $R_2$, $R_3$ and $R_5$ are hydrogen or $C_1$ - $C_7$ alkyl.

3 Claims, No Drawings

2-(5-NITRO-FURFURYLIDENE)-AMINO-BENZIMIDOLES AND FUNGICIDAL COMPOSITIONS CONTAINING THE SAME

This invention relates to new benzimidazolederivatives, and salts thereof and to compositions containing the same. The new compounds prepared by the process of our invention can be used as active ingredients in pharmaceutical compositions, in agricultural chemicals, in cosmetic products or in pesticides alone or in combination with other active ingrediens.

According to an aspect of the present invention, there are provided new compounds of the formula I,

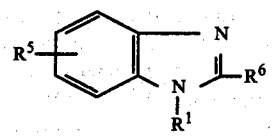

and salts thereof, wherein
$R^2$, $R^3$ and $R^5$ are hydrogen or alkyl;
$R^6$ stands for a group of the formula VII

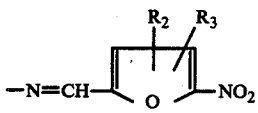

$R^1$ is hydrogen or a group of the formula VI $$-CO-NH-R^4 \quad (VI)$$

$R^4$ is an optionally substituted or unsubstituted aryl, alkyl or cycloalkyl.

The term "alkyl" relates to straight or branched chained saturated aliphatic hydrocarbon groups having 1-7, preferably 1-4 carbon atoms (e.g. methyl, ethyl, n-propyl, isopropyl, and n-butyl) which may be substituted with one or more substituents selected from the group consisting of halogen, hydroxy, alkoxy and phenyl. The term "aryl" relates to aromatic groups, e.g. phenyl, which may be substituted with one or more substituents selected from the group consisting of halogen, alkyl, and alkoxy. Preferred substituted aryl groups are the 3-chlorophenyl, and 3,4-dichlorophenyl groups. The term "cycloalkyl alkyl" relates to such groups having 3-7 carbon atoms (preferably cyclohexyl group).

The salts of the compounds of the formula I may be formed with inorganic or organic acids, e.g. hydrochloric acid, hydrobromic acid, sulphuric acid, acetic acid, formic acid, etc. The salts to be used in therapy are those formed with pharmaceutically acceptable acids.

Particularly preferred derivatives of the formula I are the following compounds: 2-(5-nitro-furfurylidene)-amino-benzimidazole; 1-methylcarbamoyl-2-(5-nitro-furfurylidene)-aminobenzimidazole;
  1-(3'-chlorophenyl-carbamoyl)-2-(5-nitro-furfurylidene)-amino-benzimidazole;
  1-(3',4'-dichlorophenyl-carbamoyl)-2-(5-nitro-furfuryl-idene)-amino-benzimidazole;
  1-cyclohexyl-carbamoyl-2-(5-nitro-furfurylidene)-amino-benzimidazole;
  2-(5'-nitro-furfurylidene)-amino-5-methyl-benzimidazole;
  1-methylcarbamoyl-2-(5'-nitro-furfurylidene)-amino-5-methyl-benzimidazole;
  1-(3''-chlorophenyl-carbamoyl)-2-(5'-nitro-furfurylidene)-amino-5-methyl-benzimidazole;
  1-(3'',4''-dichlorophenyl-carbamoyl)-2-(5'nitro-furfurylidene)-amino-5-methyl-benzimidazole;
  1-cyclohexyl-carbamoyl-2-(5'-nitro-furfurylidene)-amino-5-methyl-benzimidazole.

The process for the preparation of compounds of the formula I and salts thereof, wherein $R^1$, $R^2$, $R^3$, $R^4$, $R^5$ and $R^6$ have the same meaning as stated above,

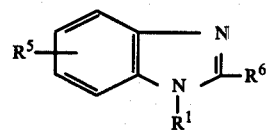

comprises
(a.) reacting a compound of the formula II

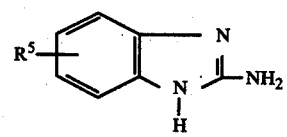

with an acylating agent or with a compound of the formula III

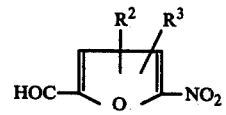

or its reactive derivative; or
(b.) reacting a compound of the formula IV

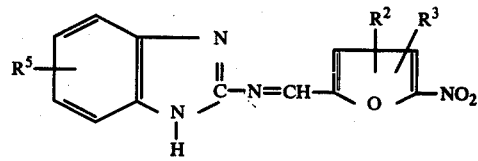

with a reactive acid derivative capable of forming a group of the formula VI, $$-CO-NH-R^4 \quad (VI)$$

preferably an isocyanate,
and, if desired converting a compound of the formula I thus obtained into its salts, or setting free the same from its salts.

According to a preferred embodiment of procedure (a.) a compound of the formula II preferably 2-amino-benzimidazole is reacted with an aldehyde of the formula III, preferably with the 5-nitro-furaldehyde or with a reactive derivative thereof, preferably with an appropriate acylate e.g. the 5-nitro-furfurylidene diacetate or dipropionate. The process may be carried out preferably in an organic solvent. As organic solvent acetic anhydride can be used. The process may be carried out at room temperature or under mild heating.

According to a preferred embodiment of procedure (b), the compound of the formula IV is reacted with an isocyanate of the formula V (R⁴—NCO). The process may be carried out preferably in the presence of an organic solvent such as, as aromatic hydrocarbons (e.g. toluene), or halogenated hydrocarbones (e.g. chloroform.)

The process may be carried out at room temperature or under mild heating preferably in the presence of a basic substance, such as triethylamine.

The compounds of the formula I may be converted into their salts in a conventional manner.

The compounds of the formula I, and their salts possess valuable fungicidal properties and may be used, therefore in human and veterinary therapy, and also in agriculture.

According to a further feature of the present invention, there are provided pharmaceutical compositions for use in human and veterinary therapy as well, comprising at least one compound of the formula I, or a salt thereof, in admixture with suitable pharmaceutically acceptable solid or liquid carriers or diluents.

The pharmaceutical compositions may be finished in the form of solutions, suspensions, emulsions, tablets, dragées, powder mixtures, ointments or granules. The compositions contain conventional carriers used in pharmacy, (e.g. starch, talc, calcium carbonate, magnesium stearate, water, polyalkylene glycols, etc.)

According to a still further feature of the present invention, there are provided desinfectants, comprising at least one compound of the formula I and salts thereof. The said desinfectants are preferably formulated in the form of aqueous solutions. Such aqueous solutions contain about 1% of a compound of the formula I or a salt thereof and are particularly suitable for disinfecting swimming pools, or other large objects liable to fungal infections.

According to a still further feature of the present invention, there are provided pesticidal compositions, comprising at least one compound of the formula I or the salts thereof, in admixture with suitable inert, solid or liquid carriers or diluents.

The said pesticides may be finished as dusting powders, sprays, granules, emulsifiable concentrates, etc. The compositions contain carriers, and diluents generally used in the formulation of pesticides. The compositions may also contain other active agents or other additives.

The pesticides contain from about 0.001% about 95% of the active ingredient of the formula I.

The pesticidal compositions of the present invention exhibit particularly strong activity against fungi belonging to the Fusarium, Basithiomycetes or Helmithosporium family. The composition may be particularly preferably applied in wheat plants against Tilletia tritici, in rye plants against Fusarium nivale, and in sugar beet plants against Cerospora baticola. The compositions may be advantageously used for seed dressing.

According to a still further feature of the present invention, there are provided cosmetical compositions comprising as active ingredient at least one compound of the formula I or a salt thereof.

Further details of the present invention are to be found in the Examples, without limiting the scope of the invention to the Examples.

EXAMPLE 1

200 g (1.5 mole) of 2-amino-benzimidazole are suspended in 1200 ml of acetone, whereupon 265 g of 5-nitro-furaldehyde are added under intensive stirring. The crystalline reaction mixture is stirred at room temperature for 2 hours while 600 ml of acetone are added. The precipitated crystals are filtered off, washed with 1 l of acetone and dried in vacuo at 40° C. to 60° C. Thus 325 g of 2-(5-nitro-furfurylidene)-amino-benzimidazole are obtained.

| Analysis $C_{12}H_8N_4O_3$ | calculated | found |
|---|---|---|
| C % | 56.2 | 56.3 ± 1 |
| H % | 3.01 | 3.3 ± 0.3 |
| N % | 21.85 | 21.57 |

EXAMPLE 2

51.2 g of 2-(5-nitro-furfurylidene)-amino-benzimidazole are dissolved in a mixture of 80 ml of dimethylformamide and 120 ml of toluene, whereupon 11.4 g (0.2 mole) methylisocyanate are slowly added. The reaction mixture is stirred at room temperature for 7 hours, whereupon it is cooled to 0° C., washed with 50 ml of toluene and dried in vacuo at 40° C. to 60° C. Thus 34 g of 1-methylcarbamoyl-2-(5-nitro-furfurylidene) amino-benzimidazole are obtained. Mp.: 170°–171° C.

| Analysis: $C_{14}H_{11}N_5O_4$ | calculated | found |
|---|---|---|
| C % | 53.8 | 53. ± 0.9 |
| H % | 3.51 | 3.3 ± 0.3 |
| N % | 22.4 | 21.7 ± 0.3 |

EXAMPLE 3

51.2 g of 2-(5-nitro-furfurylidene)-amino-benzimidazole are dissolved in a mixture of 120 ml of chloroform and 80 ml of dimethylformamide, whereupon 30.6 g (0.2 moles) of 3-chlorophenyl-isocyanate are slowly added. The crystalline reaction mixture is stirred at room temperature for 7 hours while a mixture of 40 ml of dimethylformamide and 60 ml of chloroform are added. The precipitated crystals are filtered off, washed with 100 ml of chloroform and dried in vacuo at 40° C. to 60° C. Thus 54 g of 1-(3'-chlorophenyl-carbamoyl)-2-(5-nitro-furfurylidene)-amino-benzimidazole are obtained. Mp.: 210°–212° C.

| Analysis: $C_{19}H_{12}N_5O_4Cl$ | calculated | found |
|---|---|---|
| C % | 56.1 | 55.02 |
| H % | 2.95 | 2.95 |
| N % | 17.1 | 16.89 |

EXAMPLE 4

51.2 g (0.2 moles) 2-(5-nitro-furfurylidene)-amino-benzimidazole are stirred in a mixture of 120 ml of chloroform and 80 ml of dimethylformamide, whereupon 37.6 g (0.2 moles) of powdered 3.4-dichlorophenyl-isocyanate are added. The crystalline reaction mixture is stirred at room temperature for 7 hours while a mixture of 40 ml of dimethylformamide and 60 ml of chloroform are added. The precipitated crystals are filtered off, washed with 100 ml of chloroform and dried in vacuo at 40° C. to 60° C. Thus 70 g of 1-(3',4'-dichlorophenyl-carbamoyl)-2-(5-nitro-furfurylidene)-amino-benzimidazole are obtained. Mp.: 202°–204° C.

| Analysis: $C_{19}H_{12}N_5O_4Cl_2$ | | |
|---|---|---|
| | calculated | found |
| C % | 51.8 | 51.53 |
| H % | 2.98 | 2.98 |
| N % | 15.7 | 15.78 |

EXAMPLE 5

25.1 g (0.1 mole) 2-(5-nitro-furfurylidene)-amino-benzimidazole are stirred in a mixture of 80 ml of dimethylformamide and 120 ml of methyl-ethyl-ketone, whereupon 12.6 g (0.1 mole) cyclohexylisocyanate are added. The reaction mixture is stirred for 6 hours at 40° C. to 45° C., whereupon next day it is cooled to 0° C., filtered off, washed with 20 ml of methyl-ethyl-ketone and dried in vacuo at 40° C. to 60° C. Thus 23 g of 1-cyclohexyl-carbamoyl-2-(5-nitro-furfurylidene)-aminobenzimidazole are obtained. Mp.: 198°–200° C.

| Analysis: $C_{19}H_{19}N_5O_4$ | | |
|---|---|---|
| | calculated | found |
| C % | 60.1 | 58.6 |
| H % | 4.99 | 4.72 |
| N % | 18.4 | 18.7 |

EXAMPLE 6

14.7 g (0.1 mole) of 2-amino-5-methyl-benzimidazole are suspended in 20 ml of acetone, whereupon 17.6 g of 5-nitro-furaldehyde are added under intensive stirring. The crystalline reaction mixture is stirred at room temperature for 2 hours, while 80 ml of acetone are added. The precipitated crystals are filtered off, washed with acetone and dried in vacuo at 40° C. to 60° C. Thus 20 g of 2-(5'-nitro-furfurylidene)-amino-5-methyl-benzimidazole are obtained. Mp.: 160°–162° C.

EXAMPLE 7

5.3 g (0.02 moles) of 2-(5'-nitro-furfurylidene)-amino-methyl-benzimidazole are stirred in a mixture of 30 ml of toluene and 20 ml of dimethylformamide, whereupon 1.3 ml of methylisocyanate are added. The reaction mixture is stirred at room temperature for 6 hours, the next day it is cooled to 0° C., washed with toluene and dried in vacuo at 40° C. to 60° C. Thus 3.4 g of 1-methyl-carbamoyl-2-(5'-nitro-furfurylidene)-amino-5-methyl-benzimidazole are obtained. Mp.: 179°–181° C.

EXAMPLE 8

5.4 g (0.002 moles) of 2-(5'-nitro-furfurylidene)-amino-5-methyl-benzimidazole are stirred in a mixture of 20 ml of dimethylformamide and 30 ml of chloroform, whereupon 3 g (0.02 moles) of 3-chlorophenylisocyanate are slowly added under stirring. The reaction mixture is stirred at room temperature for 6 hours. After cooling, the product is filtered off, washed with chloroform and dried. Thus 3.6 g of 1-(3''-chlorophenyl-carbamoyl)-2-(5'-nitro-furfurylidene)-amino-5-methyl-benzimidazole are obtained. Mp.: 160°–164° C.

EXAMPLE 9

5.4 g (0.02 moles) of 2-(5'-nitro-furfurylidene)-amino-5-methyl-benzimidazole are stirred in a mixture of 20 ml of dimethylformamide and 30 ml of dimethylketone, whereupon 3.2 g 3,4-dichlorophenylisocyanate are added, under stirring. The reaction mixture is stirred at room temperature for 6 hours. After cooling, the product is filtered off, washed with dimethylketone and dried. Thus 6.1 g 1-(3'',4''-dichlorophenyl-carbamoyl)-2-(5'-nitro-furfurylidene)-amino-5-methyl-benzimidazole are obtained. Mp.: 165°–167° C.

EXAMPLE 10

5.4 g (0.02 moles) of 2-(5'-nitro-furfurylidene)-amino-5-methyl-benzimidazole are stirred in a mixture of 20 ml of dimethylformamide and 30 ml of methyl-ethyl-ketone, whereupon 2.8 ml of cyclohexylisocyanate are added. The reaction mixture is stirred at room temperature for 6 hours. After cooling the product is filtered off, washed with methyl-ethyl-ketone and dried. Thus 4.4 g of 1-cyclohexyl-carbamoyl-2-(5'-nitro-furfurylidene) amino-5-methyl-benzimidazole are obtained. Mp.: 172°–175° C.

What we claim is:

1. A compound of the formula I

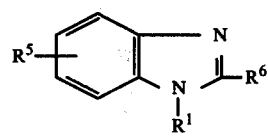

wherein
$R^5$ is hydrogen or $C_1$ to $C_7$ alkyl and
$R^6$ stands for a group of the formula VII

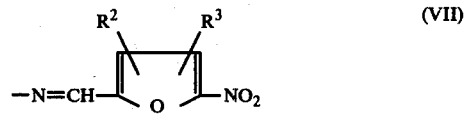

wherein $R^2$ and $R^3$ are hydrogen or $C_1$ to $C_7$ alkyl; and $R^1$ is a group of the formula VI

wherein
$R^4$ is phenyl or phenyl substituted with halogen, alkyl of 1 to 7 carbon atoms or alkoxy of 1 to 7 carbon atoms, $C_1$ to $C_7$ alkyl or $C_3$ to $C_7$ cycloalkyl, and having fungicidal properties; or a fungicidally effective salt thereof.

2. A compound as defined in claim 1 and selected from the group which consists of:
1-methyl-carbamoyl-2-(5-nitro-furfurylidene)-amino-benzimidazole;
1-(3'-chlorophenyl-carbamoyl)-2-(5-nitro-furfurylidene)-amino-benzimidazole;
1-(3',4'-dichlorophenyl-carbamoyl)-2-(5-nitro-furfurylidene)-amino-benzimidazole;
1-cyclohexyl-carbamoyl-2-(5-nitro-furfurylidene)-amino-benzimidazole;
2-(5'-nitro-furfurylidene)-amino-5-methyl-benzimidazole;
1-methyl-carbamoyl-2-(5'-nitro-furfurylidene)-amino-5-methyl-benzimidazole;
1-(3''-chlorophenyl-carbamoyl)-2-(5'-nitro-furfurylidene)-amino-5-methyl-benzimidazole;
1-(3'',4''-dichlorophenyl-carbamoyl)-2-(5'-nitro-furfurylidene)-amino-5-methyl-benzimidazole; and
1-cyclohexyl-carbamoyl-2-(5'-nitro-furfurylidene)-amino-5-methyl-benzimidazole.

3. A fungicidal composition comprising, as active ingredient, an effective amount of a compound of the formula I

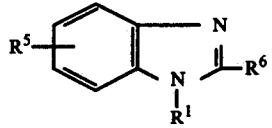
(I)

wherein $R^5$ is hydrogen or $C_1$ to $C_7$ alkyl and $R^6$ is a group of the formula VII

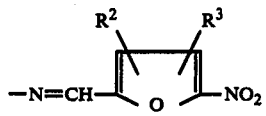
(VII)

wherein $R^2$ and $R^3$ are hydrogen or $C_1$ to $C_7$ alkyl; and
$R^1$ is a group of the formula VI

(VI)

wherein
$R^4$ is phenyl or phenyl substituted with halogen, alkyl of 1 to 7 carbon atoms or alkoxy of 1 to 7 carbon atoms, $C_1$ to $C_7$ alkyl or $C_3$ to $C_7$ cycloalkyl, and having fungicidal properties; or a fungicidally effective salt thereof in admixture with a solid or liquid carrier suitable for fungicidal application.

* * * * *